US012642455B2

(12) United States Patent (10) Patent No.: US 12,642,455 B2
Kaiser et al. (45) Date of Patent: *Jun. 2, 2026

(54) MEDICAL CAMERA ASSEMBLY COMPRISING RANGE CAMERA AND THERMOGRAPHIC CAMERA

(71) Applicant: Brainlab AG, Munich (DE)

(72) Inventors: Hagen Kaiser, Munich (DE); Kajetan Berlinger, Munich (DE)

(73) Assignee: BRAINLAB SE, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/907,879

(22) Filed: Oct. 7, 2024

(65) Prior Publication Data

US 2025/0241559 A1 Jul. 31, 2025

Related U.S. Application Data

(63) Continuation of application No. 18/139,478, filed on Apr. 26, 2023, now Pat. No. 12,138,043, which is a
(Continued)

(30) Foreign Application Priority Data

Dec. 2, 2014 (WO) ................. PCT/EP2014/076287
Apr. 28, 2015 (WO) ................. PCT/EP2015/059171

(51) Int. Cl.
*A61B 5/11* (2006.01)
*A61B 5/00* (2006.01)
(Continued)

(52) U.S. Cl.
CPC .......... *A61B 5/1128* (2013.01); *A61B 5/0035* (2013.01); *A61B 5/0064* (2013.01);
(Continued)

(58) Field of Classification Search
CPC ... A61B 5/1128; A61B 5/0035; A61B 5/0064; A61B 5/0077; A61B 5/015; A61B 5/11;
(Continued)

(56) References Cited

U.S. PATENT DOCUMENTS 6,754,370 B1 * 6/2004 Hall-Holt ............... G01B 11/25
356/3
7,519,210 B2 4/2009 Hirsch
(Continued)

FOREIGN PATENT DOCUMENTS

EP 2779624 A1 9/2014
GB 2418495 B 4/2010
(Continued)

OTHER PUBLICATIONS

Skala, Karolj, et al. "4D thermal imaging system for medical applications." Periodicum biologorum 113.4 (2011): 407-416. (Year: 2011).*

(Continued)

*Primary Examiner* — Sean D Mattson
(74) *Attorney, Agent, or Firm* — Tucker Ellis LLP

(57) ABSTRACT

A camera assembly for use in medical tracking applications includes a range camera and a thermographic camera. The range camera is configured to acquire a first point cloud of at least a portion of an object at a first moment in time and a second point cloud of at least the portion of the object at a second moment in time. The thermographic camera is configured to acquire a first thermal image of at least the portion of the object at the first moment in time and a second thermal image of at least the portion of the object at the second moment in time. The assembly includes a processor configured to calculate a movement of at least the portion of the object between the first moment of time and the second moment of time based on the first point cloud and the second (Continued)

Figure 1:
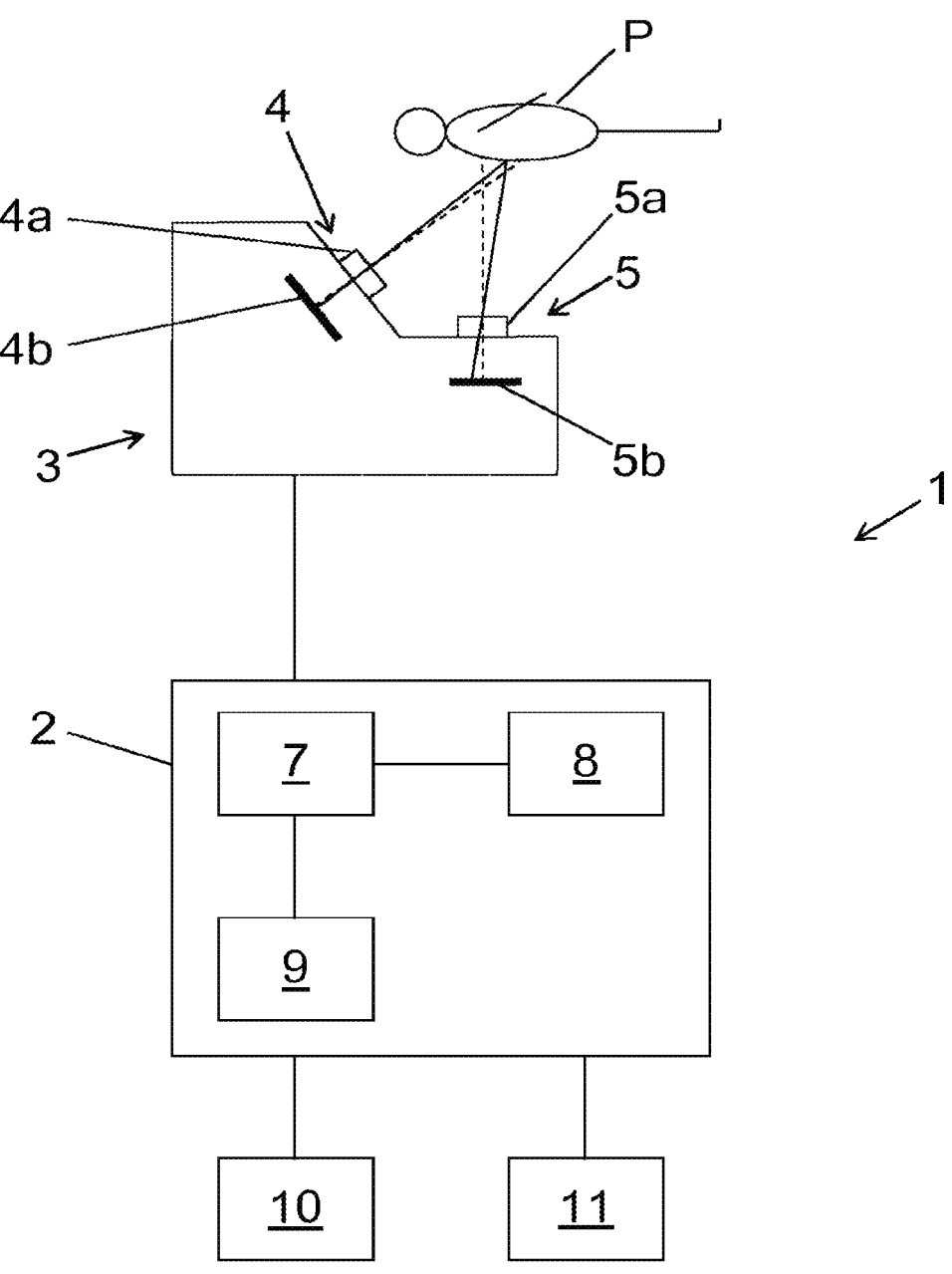

point cloud with additional information acquired from the first and second thermal images.

20 Claims, 4 Drawing Sheets

Related U.S. Application Data continuation of application No. 16/953,803, filed on Nov. 20, 2020, now Pat. No. 11,666,250, which is a continuation of application No. 15/308,962, filed as application No. PCT/EP2015/059542 on Apr. 30, 2015, now Pat. No. 10,874,331.

(51) Int. Cl.

| | | |
|---|---|---|
| *A61B 5/01* | (2006.01) |
| *A61B 5/113* | (2006.01) |
| *G01J 5/00* | (2022.01) |
| *G06T 7/00* | (2017.01) |
| *G06T 7/33* | (2017.01) |
| *G06T 7/70* | (2017.01) |
| *G01J 5/48* | (2022.01) |
| *H04N 13/00* | (2018.01) |
| *H04N 13/239* | (2018.01) |

(52) U.S. Cl.

CPC ........... *A61B 5/0077* (2013.01); *A61B 5/015* (2013.01); *A61B 5/11* (2013.01); *A61B 5/113* (2013.01); *A61B 5/7292* (2013.01); *G01J 5/00* (2013.01); *G06T 7/0012* (2013.01); *G06T 7/33* (2017.01); *G06T 7/70* (2017.01); *A61B 2576/00* (2013.01); *G01J 2005/0077* (2013.01); *G01J 5/48* (2013.01); *G06T 2207/10028* (2013.01); *G06T 2207/10048* (2013.01); *H04N 2013/0081* (2013.01); *H04N 13/239* (2018.05)

(58) Field of Classification Search

CPC ..... A61B 5/113; A61B 5/7292; A61B 5/1114; A61B 2576/00; A61B 2576/02; A61B 2560/0223; G01J 5/00; G01J 5/10; G01J 5/48; G01J 2005/0077; G06T 7/0012; G06T 7/33; G06T 7/70; G06T 2207/10028; G06T 2207/10048; H04N 13/239; H04N 2013/0081; H04N 13/204; G16H 30/40; A61N 5/1049; A61N 5/1068; A61N 5/1069

See application file for complete search history.

(56) References Cited

U.S. PATENT DOCUMENTS

| | | | |
|---|---|---|---|
| 7,734,077 B2 | 6/2010 | Hirsch et al. |
| 10,874,331 B2 * | 12/2020 | Kaiser | A61B 5/015 |
| 11,666,250 B2 * | 6/2023 | Kaiser | A61B 5/1114 |
| | | | 600/476 |
| 12,138,043 B2 * | 11/2024 | Kaiser | A61B 5/1128 |
| 2002/0173723 A1 | 11/2002 | Lewis |
| 2004/0023612 A1 | 2/2004 | Kriesel |
| 2007/0247517 A1 | 10/2007 | Zhang |
| 2010/0135550 A1 | 6/2010 | Arnon |
| 2010/0172567 A1 * | 7/2010 | Prokoski | A61B 5/418 |
| | | | 348/47 |
| 2010/0284591 A1 | 11/2010 | Arnon et al. |
| 2011/0021944 A1 * | 1/2011 | Arnon | A61B 5/015 |
| | | | 600/3 |
| 2011/0118608 A1 | 5/2011 | Lindner et al. |
| 2012/0078113 A1 | 3/2012 | Whitestone et al. |
| 2012/0226152 A1 | 9/2012 | Porikli |
| 2012/0289850 A1 * | 11/2012 | Xu | A61B 5/015 |
| | | | 600/529 |
| 2012/0307046 A1 | 12/2012 | Lundberg |
| 2016/0006951 A1 | 1/2016 | Moghadam |

FOREIGN PATENT DOCUMENTS

| | | |
|---|---|---|
| WO | 2014127431 A1 | 8/2014 |
| WO | 2016086976 A1 | 6/2016 |

OTHER PUBLICATIONS

Bilodeau, Guillaume-Alexandre, et al. "Body temperature estimation of a moving subject from thermographic images." Machine Vision and Applications 23.2 (2012): 299-311. (Year: 2012).*

Weinmann, Martin, et al. "Thermal 3D mapping for object detection in dynamic scenes." ISPRS Annals of the Photogrammetry, Remote Sensing and Spatial Information Sciences 2 (2014): 53-60. (Year: 2014).*

International Search Report for PCT/EP2015/059542, Date of Mailing Aug. 12, 2015, pp. 1-6.

Written Opinion of the International Searching Authority for PCT/EP2015/059542, pp. 1-11.

M. Calonder et al., "BRIEF: Computing a Local Binary Descriptor Very Fast", IEEE Transactions on Pattern Analysis and Machine Intelligence, vol. 34, issue No. 07, Jul. 2012, pp. 1281 to 1298.

C.Lu et al., "Fast and Globally Convergent Pose Estimation from Video Images" published in IEEE Transactions on Patent Analysis and Machine Intelligence, vol. 22, No. 6, Jun. 2000, pp. 610 to 622.

M. Calonder et al., "BRIEF: Computing a Local Binary Descriptor Very Fast", Computer Vision Laboratory, I&C Faculty, pp. 1-29, Lausanne, Switzerland.

* cited by examiner

S01   acquire first
      point cloud and first
      thermal image

S02   acquire second point
      cloud and second
      thermal image

S03   find corresponding
      points in thermal
      images

S04   obtain correspon-
      dences from point
      clouds based on
      corresponding points S05   match
      correspondences

MEDICAL CAMERA ASSEMBLY COMPRISING RANGE CAMERA AND THERMOGRAPHIC CAMERA

RELATED APPLICATION DATA

This application is a continuation of U.S. patent application Ser. No. 18/139,478, filed on Apr. 26, 2023. Application Ser. No. 18/139,478 is a continuation of U.S. patent application Ser. No. 16/953,803, filed on Nov. 20, 2020. Application Ser. No. 16/953,803 is a continuation of U.S. patent application Ser. No. 15/308,962, filed on Nov. 14, 2016. Application Ser. No. 15/308,962 is a national phase application of International Application No. PCT/EP2015/059542, filed Apr. 30, 2015, published in the English language, which claims priority to International Application No. PCT/EP2015/059171 filed on Apr. 28, 2015, and International Application No. PCT/EP2014/076287, filed on Dec. 2, 2014. The entireties of the aforementioned applications are incorporated herein by reference.

The present invention relates to a camera assembly for use in medical tracking applications, to a data processing method, performed by a computer, for tracking at least a part of a surface of a patient and to a corresponding computer program and system.

Many medical applications require recognizing the movement of a patient, or of at least a part of a patient. There are many approaches for determining this movement, that is for tracking the patient, in the art. One approach uses a marker which is attached to the patient and a system which tracks the position of the marker in space. Another approach uses a stereoscopic optical camera to capture the three-dimensional surface of the patient over time and matches the three-dimensional images of the surfaces in order to calculate a transformation between the positions of the surface. One implementation of this approach uses light which is projected onto the surface in a particular pattern. Yet another approach is to use a range camera, more generally referred to as range imager, which acquires a point cloud, the points corresponding to points on the surface, which are therefore also referred to as surface points. Typical output data of a range camera is a two-dimensional array of depth values, which represent the distance of the imaged surface point from the range camera. The two-dimensional array corresponds to pixels of an image sensor. The point clouds obtained at different points in time are then matched in order to obtain a transformation between the point clouds which equals the transformation, or movement, of the patient.

A problem of the approach using a range camera is that it might not be possible to unambiguously match the point clouds. This occurs in particular if the imaged surface is flat, curved in one dimension only or exhibits a symmetry, such as a rotational symmetry.

The present invention aims at improving a movement detection using a range camera.

The system, the method and the program are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

A camera assembly, or camera system, for use in medical tracking applications according to the present invention comprises a range camera and a thermographic camera in a fixed relative position. In other words, the range camera and the thermographic camera are arranged with a defined and/or known distance and defined and/or known viewing directions relative to each other. The thermographic camera captures a thermal image which comprises additional information over the information of a range image, or point cloud, determined by use of the range camera.

The thermographic camera comprises a lens system which images at least the part of the surface which comprises a point onto a sensor which converts radiation emitted from the point into two-dimensional thermal image data. The properties of the lens system, such as its focal length and any distortions caused by the lens system, are preferably known to a method or a control unit which analyses the thermal image data. Optionally, the distortions are corrected within the camera before the two-dimensional thermal image is provided by the camera. The output of the camera can be stored in a data storage and subsequently acquired from the data storage.

In a thermal image, the pixels do not represent the colour of a point in the visible spectrum, but rather a temperature or temperature distribution emitted from the point. Since each point emits a range of temperatures up to a maximum temperature, a pixel of a thermal image can for example represent this maximum temperature of the point. In this document, a thermal image preferably only represents the thermal radiation emitted from the surface of the patient's body in a non-visible spectrum. A thermal image can only be effectively presented to a human eye if frequency mapping is performed. This is often referred to as false-colour representation.

The advantage of a thermal image is that the spectrum of the thermal radiation is independent of ambient conditions, such as illumination, and the optical properties of the surface, so even if a large area of the surface has a flat or an ambiguous shape, thus resulting in a point cloud with neighbouring pixels having the same depth, it may exhibit a particular pattern in its thermal radiation, such that corresponding points in point clouds obtained by the range camera can be found.

In one embodiment, the thermal two-dimensional images represent wavelengths between 8 $\mu$m and 14 $\mu$m. This range corresponds to typical temperatures for the surface of a patient's body. The two-dimensional thermal images preferably do not represent wavelengths in the near infrared spectrum. The near infrared spectrum is typically understood to extend as far as wavelengths of 2.5 $\mu$m or 3 $\mu$m.

The present invention does allow to not only utilize the point clouds to determine a movement of the patient, but additional information comprised in the thermal images. A thermal image of human skin yields many recognizable features due to many different equithermal regions, which are mainly caused by a non-uniform distribution of the blood vessels inside the human body. This means that different points on the surface of the patient's body have different thermal features or signatures, such that they can be distinguished irrespective of the shape of the surface. The additional information comprised in the thermal images can thus be used to identify correspondences in or from the point clouds. The matching process can then be reduced to matching the correspondences, which is computationally less complex and unambiguous irrespective of the shape of the surface.

Finding correspondences in the point clouds for example comprises finding corresponding pixels in the first and second thermal images. Corresponding pixels, which image the same surface point, are found by searching for a particular thermal feature or characteristic in both thermal images. This can for example involve finding pixels showing the same temperature or pixels having the same descriptor. It shall be noted that corresponding pixels are not necessarily native pixels in the thermal images, but could be interpolated pixels.

Once the positions of the corresponding pixels in the thermal images have been found, the lines in space on which the corresponding surface point lies at the first point in time and the second point in time can be calculated from the characteristics of the thermographic camera. The position of the imaged surface point on the straight line can be determined from the corresponding point cloud, for example by finding the point in the point cloud which lies on the straight line and is closest to the thermographic camera. If there is no such point in the point cloud, a point can be interpolated from at least some of the points of the point cloud.

In one embodiment, the camera assembly further comprises a common housing in which the range camera and the thermographic camera are arranged. This assures that the range camera and the thermographic camera remain in their fixed relative position.

The range camera is for example a stereo camera, a structured light 3D scanner, a time-of-flight camera or a laser scanner. A stereo camera typically comprises two two-dimensional cameras, such as optical cameras, with a certain offset. The location of a point relative to the stereo camera is obtained based on the fact that the position of the point in the two two-dimensional images depends on the position of the point relative to the camera. A structured light 3D scanner projects a particular light pattern onto the surface, captures the reflected light by a camera and determines the three-dimensional shape of the surface from the difference of the projected light pattern and the image of the reflected light pattern in the output image of the camera.

A time-of-flight camera emits a light pulse onto the surface and determines the three-dimensional structure of the surface from the time-of-flight of the light pulse to the surface and back onto the pixels of a two-dimensional camera. A laser scanner uses a similar principle, but scans the surface point by point.

In one embodiment, the camera assembly comprises a storage unit which stores calibration information which represents the relative position between the range camera and the thermographic camera. Due to tolerances in manufacturing of the camera assembly, the relative position between the range camera and thermographic camera may vary among multiple camera assemblies. The relative position between the range camera and the thermographic camera can however be measured, for example by imaging a phantom, and then be stored as the calibration information. The calibration information can then be used when the output data of the range camera and the thermographic camera are analysed.

In one embodiment, the camera assembly comprises a processing unit. The processing unit is configured to acquire, at a first point in time, a first point cloud from the range camera and a first thermal image from the thermographic camera. The processing unit is further configured to acquire, at a second point in time later than the first point of time, a second point cloud from the range camera and a second thermal image from the thermographic camera.

The processing unit is further configured to find at least one point pair in the first and second thermal images, wherein a point pair comprises a point in the first thermal image and a point in the second thermal image and the two points correspond to the same point on the surface of an imaged object. Still further, the processing unit is configured to calculate a movement of the imaged object, such as the patient, the surface of the patient or a part of the surface, between the first and second points in time from the first point cloud, the second point cloud and the at least one point pair.

The movement is thus not only calculated based on the two point clouds, but on additional information which identifies the same point on the surface of the imaged object in the first and the second thermal image. This additional information can in particular resolve any disambiguity which might cause that the two point clouds cannot be matched correctly.

In one embodiment, the processing unit is configured to calculate the movement by matching a first reduced point cloud and a second reduced point cloud, the reduced point clouds comprising points corresponding to the point pairs.

The first reduced point cloud comprises points taken from the first point cloud and/or points calculated from the first point cloud, and the second reduced point cloud comprises points taken from the second point cloud and/or points calculated from the second point cloud.

With the point pairs being identified in the first and second thermal images, and the characteristics of the thermographic camera being known, the surface point of the imaged object must lie on a straight line having a known position relative to the thermographic camera, and therefore relative to the range camera. It is therefore possible to determine a first point in the first point cloud which lies on the straight line corresponding to the first thermal image and a second point in the second point cloud which lies on the straight line corresponding to the second thermal image. Since the point pair corresponds to the same point on the surface of the imaged object, the first point of the first point cloud and the second point of the second point cloud depict the same point on the surface of the imaged object. The first point and the second point are therefore point correspondences which should be matched into each other. The first point is added to the first reduced point cloud and the second point is added to the second reduced point cloud. In one implementation, correspondence information indicating that the first and second points correspond to each other is stored.

If a plurality of point pairs is determined from the first and second thermal images, and therefore a plurality of point correspondences in the first point cloud and the second point cloud are determined in order to generate the first reduced point cloud and the second reduced point cloud, the matching step can be reliably performed and with little computational complexity. While a point cloud typically comprises 30,000 or far more points which have to be matched if there is no additional information, the reduced point clouds typically comprise only several hundred points, thus significantly reducing the computational complexity of the matching step. In addition, the point-to-point correspondences in the reduced point clouds make the matching step unambiguous.

It shall be noted that a reduced point cloud might not be limited to points actually comprised in a point cloud, but might comprise interpolated points. So if for example a point cloud does not comprise a point lying on a straight line as derived from the corresponding thermal image, points of the point cloud, such as points close to the straight line, are interpolated in order to obtain a point which lies on the straight line.

In one embodiment, the processing unit is configured to calculate the movement by calculating the relative spatial positions of the points in the point pairs at the first point in time, thus obtaining an object point model and performing rigid fusion of the object point model with the second thermal image.

As explained for the previous embodiment, a straight line on which a surface point imaged in the first thermal image lies can be identified and the spatial position of the surface point relative to the camera assembly can be determined as the position of a point in the first point cloud which lies on this straight line or by interpolating the point from a plurality of points of the first point cloud, the interpolated point lying on this straight line. If the spatial positions of a plurality of surface points relative to the camera assembly are determined in this way, the relative spatial positions of the surface points can be calculated. In addition, the (virtual) position of the object point model relative to the camera assembly is calculated, for example as the relative position of a co-ordinate system assigned to the object point model relative to the camera assembly.

The rigid fusion now places the object point model relative to the camera assembly such that each point of the object point model lies on a straight line derived from the position of the corresponding surface point in the second thermal image and the properties of the thermographic camera. In other words, straight lines are determined for the points of the plurality of point pairs at the second point in time and the object point model is then placed such that the points of the object point model lie on the corresponding straight lines. It shall be noted that it might not be possible to position the object point model such that all points exactly lie on the corresponding straight lines, such that an optimization algorithm might be applied. Such an optimization algorithm might for example minimize the distances between the points of the object point model and the corresponding straight lines derived from the second thermal image.

It shall be noted that a point of a point pair at the first point in time is the point out of the point pair which is found in the first thermal image. In analogy, a point of a point pair at the second point in time is the point of a point pair which is found in the second thermal image.

The result of the rigid fusion is a transformation which describes how the position of the obtained object point model has to be changed such that the new position of the object point model relative to the camera assembly leads to the projection of the points of the object point model as shown in the second thermal image. This transformation therefore represents the movement of the surface of the imaged object. The rigid fusion is also referred to as 3D/2D registration.

The rigid 3D/2D fusion can for example be performed using the posit algorithm for any general perspective-n-point algorithm, such as described in the article "Fast and globally convergent pose estimation from video images" by C.-P. Lew, G. D. Hager und E. Mjolsness, published in IEEE Transactions on Patent Analysis and Machine Intelligence, Vol. 22, No. 6, June 2000.

In one embodiment, the processing unit is configured to calculate the movement by calculating the relative spatial positions of the points in the point pairs at the first point in time, thus obtaining a first object point model, calculating the relative spatial positions of the points of the point pairs at the second point in time, thus obtaining a second object point model, and performing rigid fusion of the first object point model with the second object point model. This embodiment is similar to the previous embodiment, but does not perform a 3D/2D matching at the rigid fusion, but obtains two object point models with a particular position relative to the camera assembly and then performs a 3D/3D fusion of the object point models in order to obtain a transformation between the two object point models. However, calculating the first object point model and the second point object model is as described in the preceding embodiment.

Briefly summarized, the additional information obtained from a thermal image captured by the thermographic camera allows to obtain point-to-point correspondences in the point clouds obtained from the range camera such that matching can be reduced from the whole point clouds to the point-to-point correspondences, which makes the registration more robust and significantly faster, for example by the order of 100.

As outlined above, one advantage of using thermal images is that points on the surface of a patient can be reliably detected irrespective of exterior conditions such as the illumination in the visible spectrum. There are several approaches for finding the same point on the surface of the patient in a plurality of thermal images, such as the first thermal image and the second thermal image. One approach is to assign a particular temperature to the surface point and to find a point in a thermal image which has the same temperature. A more complex approach is to not only consider the temperature of the surface point itself, but a thermal signature of an area surrounding the surface point.

In one embodiment, the method comprises the step of assigning a descriptor to a point on the surface of the patient's body. A descriptor is for example a value which is calculated from the properties of the point and optionally also from the properties of points in the vicinity of the point. A descriptor is typically used to unambiguously identify a point. In this document, a descriptor can also be a set of descriptors or descriptor values. A descriptor is for example calculated from a thermal image, for example from the properties of a pixel which represents the point on the surface and/or from the properties of pixels in the vicinity of this pixel.

One advantage of the descriptor is that it is basically invariant over time (such as for example for 1 second, 2 seconds, 5 seconds, 10 seconds, 15 seconds, 30 seconds, 60 seconds or even longer). This means that the descriptor can advantageously be used to identify pixels which show the same point on the surface of the body in the thermal images taken at different points in time.

The principles of calculating a descriptor are for example disclosed in M. Calonder, V. Lepetit, M. Özuysal, T. Trzcinski, C. Strecha, P. Fua, "BRIEF: Computing a Local Binary Descriptor Very Fast", IEEE Transactions on Pattern Analysis and Machine Intelligence, Volume 34, issue No. 07, July 2012, pages 1281 to 1298, which is incorporated by this reference.

The present invention further relates to a data processing method performed by a computer for tracking at least a part of a surface of a patient. The method comprises the steps of acquiring, at a first point in time, a first point cloud from a range camera and a first thermal image from a thermographic camera, the range camera and the thermographic camera being in a fixed relative position, and acquiring, at a second point in time later than the first point in time, a second point cloud from the range camera and a second thermal image from the thermographic camera. The method further comprises the step of finding at least one point pair in the first and second thermal images, wherein a point pair comprises a point in the first thermal image and a point in the second thermal image which correspond to the same point on the surface of the patient.

The method further comprises the step of calculating movement of the surface of the patient between the first and second points in time from the first point cloud, the second point cloud and the at least one point pair.

In one embodiment, calculating the movement involves calibration information which represents the relative position between the range camera and the thermographic camera. As explained above with reference to the camera assembly, the additional information comprised in the thermal images is for example used to identify corresponding points in the point clouds obtained by the range camera. This requires the relative position between the range camera and the thermographic camera to be known such that the information obtained from the thermal images can be combined with the points clouds. Since the relative position between the range camera and the thermographic camera may vary due to manufacturing tolerances, the actual relative position can be determined, for example by a calibration using a phantom to be imaged, and stored as the calibration information.

In one embodiment, calculating the movement involves matching a first reduced point cloud and a second reduced point cloud, the reduced point clouds comprising points corresponding to the point pairs.

In one embodiment, calculating the movement involves calculating the relative spatial positions of the points of a plurality of point pairs at the first point in time, thus obtaining an object point model, and performing rigid fusion of the object point model with the second thermal image.

In one embodiment, calculating the movement involves calculating the relative spatial positions of the points of a plurality of point pairs at the first point in time, thus obtaining a first object point model, calculating the relative spatial positions of the points of the plurality of point pairs at the second point of time, thus obtaining a second object point model, and performing rigid fusion of the first object point model with the second object point model.

The method and the embodiments described above correspond to the camera assembly and the embodiments thereof, which are described in detail. Repeating the details is therefore omitted. The present invention also relates to a computer program embodied on a non-transitory computer-readable medium which, when running on a computer or loaded onto a computer, causes the computer to perform any one or more of the data processing methods described above.

The present invention further relates to a system for tracking at least a part of a surface of a patient, comprising a computer on which the aforementioned program is stored and/or run.

The method in accordance with the invention is a data processing method. The data processing method is preferably performed using technical means, for example a computer. The data processing method is preferably constituted to be executed by or on a computer and for example is executed by or on the computer. For example, all the steps or merely some of the steps (i.e. less than the total number of steps) of the method in accordance with the invention can be executed by a computer. The computer for example comprises a processor and a memory in order to process the data, for example electronically and/or optically. The calculating steps described are for example performed by a computer. Determining steps or calculating steps are for example steps of determining data within the framework of the technical data processing method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a data processing method)

the scenario in which the data are determined by the data processing unit, method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the data processing method or program, for example from another program, a previous method step or a data storage medium, for example for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The method in accordance with the invention is preferably at least partly executed by a computer, i.e. all the steps or merely some of the steps (i.e. less than the total number of steps) of the method in accordance with the invention can be executed by a computer.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there are a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

In particular, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to positioning a tool relative to the medical implant, which may be outside the patient's body. For this reason alone, no surgical or therapeutic activity and in particular no surgical or therapeutic step is necessitated or implied by carrying out the invention.

The present invention can for example be used in combination with the Vero® or ExacTrac® systems offered by the applicant. A movement of a patient can be determined as described herein, and if this movement exceeds a particular threshold, the aforementioned systems can be triggered to find the current position of the user, for example by taking two x-ray images. However, the present invention can be used in combination with any medical system or method which requires detection of a movement of a patient.

Figure 2:
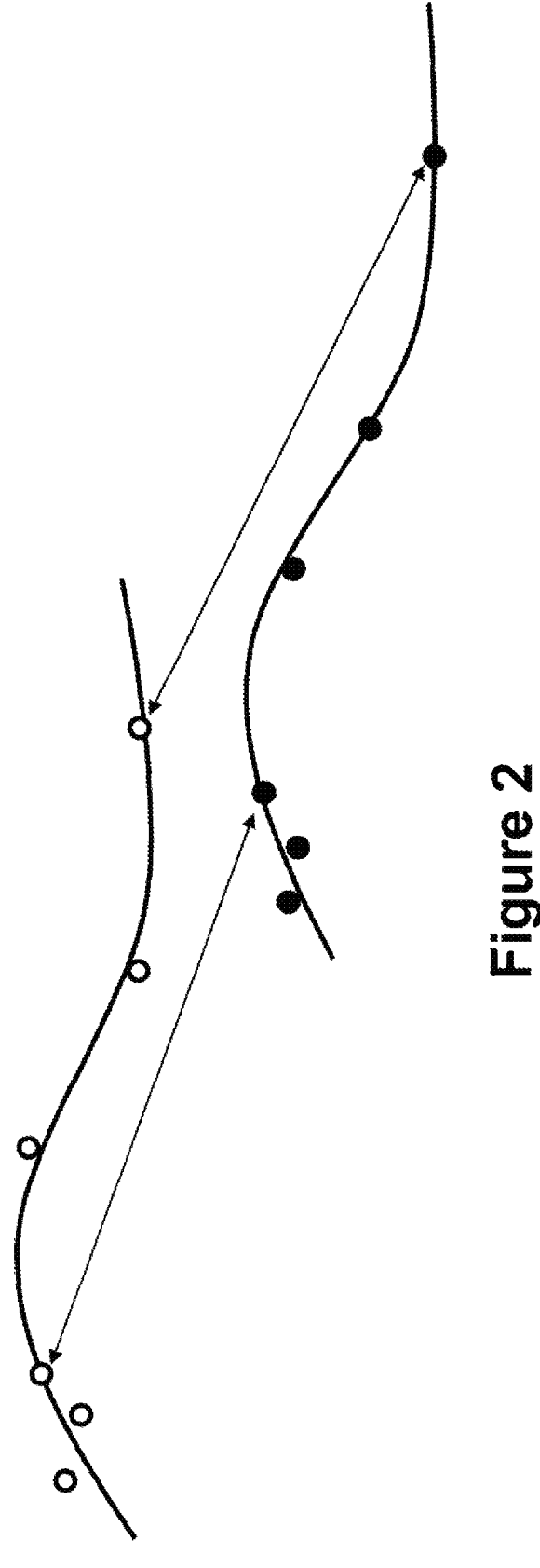
Figure 3:
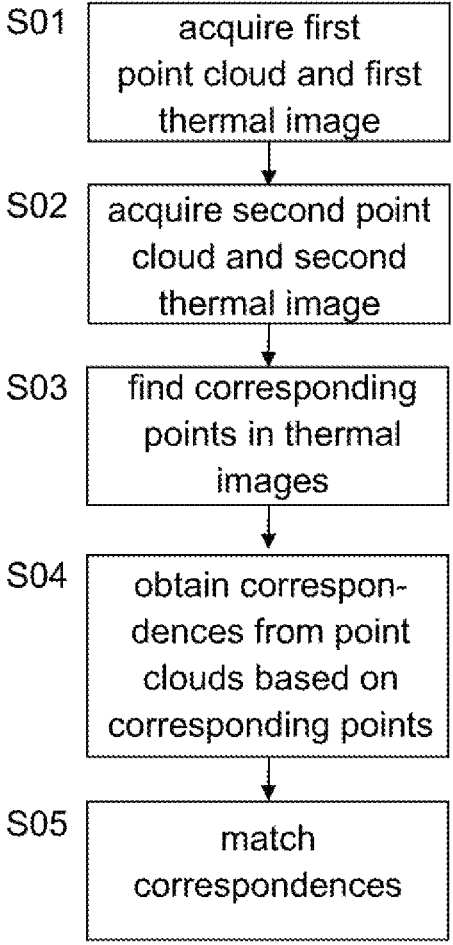

In the following, the invention is described with reference to the enclosed figures which represent preferred embodiments of the invention. The scope of the invention is not however limited to the specific features disclosed in the figures, which show:

FIG. 1 a tracking system comprising a camera assembly and a computer;

FIG. 2 two point clouds to be registered;

FIG. 3 a flow diagram of a first approach for tracking movement; and

Figure 4:
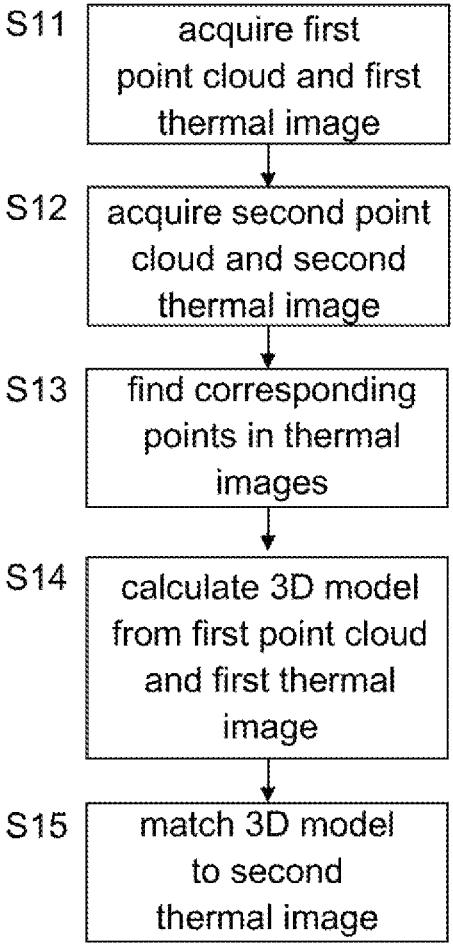

FIG. 4 a flow diagram of a second approach for tracking movement.

FIG. 1 schematically shows a tracking system 1 for tracking at least a part of a surface of a patient P. The tracking system 1 comprises a computer 2 and a camera assembly 3. The camera assembly 3 and the patient P are positioned relative to each other such that the camera assembly 3 captures at least a part of the surface of the patient P. A point on the surface of the patient P is also referred to as surface point.

The camera assembly 3 comprises a range camera 4 and a thermographic camera 5. The range camera 4 in the present embodiment is a time-of-flight camera having a light source (not shown), a lens system 4a and a sensor 4b. The thermographic camera 5 comprises a lens system 5a and a sensor 5b. The lens systems 4a and 5a guide incident light or thermal radiation, respectively, onto the sensors 4b and 5b, respectively. The sensor 5b creates a two-dimensional thermal image which preferably represents wavelengths of between 8 μm and 14 μm.

In the present example, the sensor 5b is a two-dimensional array of sensor cells which convert incident thermal radiation into a voltage which corresponds to the temperature of the corresponding point on the surface of the patient's body. The temperature is typically derived from the wavelength of the maximum within the spectrum of the incident infrared radiation.

The range camera 4 measures, for each pixel, the time between emitting light by the light source of the range camera 4 and receiving the emitted light, which was reflected by the patient P, by the sensor 4b. The range camera 4 therefore measures the time of flight, which corresponds to the distance between the camera 4 and the imaged point on the surface of the patient P. The output of the range camera 4 is a two-dimensional array of distances. For the sake of simplicity, the elements of the array are referred to as pixels and the output of the range camera is referred to as range image.

The lens system 5a has a characteristic axis similar to the optical axis of a camera which captures an image in the visible spectrum. In analogy, the lens system 4a of the range camera also has a characteristic axis. The characteristic axes are shown as dashed lines in FIG. 1. As can be seen from FIG. 1, the two cameras 4 and 5 have different characteristic axes and therefore different viewing directions, which, however, is not mandatory. Since the relative position between the range camera 4 and the thermographic camera 5 is fixed, the relative position between the characteristic axes is also fixed.

Thermal radiation emitted from a point on the patient P is guided onto a pixel of the sensor 5b in accordance with the spatial location of the point on the surface of the patient's body and the properties of the lens system 5a. In analogy, light reflected by a point on the patient P is guided onto a pixel of the sensor 4b in accordance with the spatial location of the point on the surface of the patient's body and the properties of the lens system 4a. For each pixel in a range image or a thermal image, a straight line can be calculated, from the properties of the camera, such that all points which lie on this line would be imaged by said pixel.

The computer 2 comprises a central processing unit 7, a memory unit 8 and an interface 9. The memory unit 8 stores program data and/or working data, such as the image datasets acquired from the camera assembly 3. The computer is connected to the input device 10, the output device 11 and/or the camera assembly 3 via the interface 9.

The computer 2 acquires the two images, which were captured using the sensors 4b and 5b, from the camera assembly 3. The computer 2 is provided with the properties of the range camera 4 and the thermographic camera 5 as well as the relative position between the two cameras, such that for each pixel in each of the two images, the computer 2 knows or is able to calculate the line on which a point imaged by said pixel is located.

Since the range camera 4 determines, for each pixel, the distance of the point on the surface of the patient which is imaged by this pixel, the computer 2 can calculate a point cloud of the points imaged in the range image, the point cloud comprising the location of each imaged point relative to the range camera 4. As an alternative, the point cloud is calculated within the range camera 4 and acquired by the computer 2.

FIG. 2 shows a first point cloud and a second point cloud acquired at first and second points in time, respectively, wherein the second point in time is later than the first point in time. The points of the first point cloud are shown as circles, while the points of the second point cloud are shown as filled circles. While the point clouds are shown in two dimensions only in FIG. 2, they actually comprise the location of the points relative to the range camera 4 in three dimensions. The surface of the patient P is shown in FIG. 2 as curves which are fitted to the respective point clouds.

As can be seen from FIG. 2, the point clouds are shifted relative to each other, which means that the patient P has moved between the first and second points in time. In order to detect the movement of the patient P, the first and second point clouds have to be matched with each other. However, this is a time consuming task due to the large number of points in each point cloud, which can be as much as several hundred thousand. The matching process is therefore computationally complex. In addition, the matching result might be ambiguous, for example if the surface of the patient P were flat.

The present embodiment therefore finds and uses correspondences in or from the point clouds for detecting the movement of the patient P. Correspondences in the two point clouds are connected by arrows in FIG. 2. In the example shown in FIG. 2, the correspondences are points in the two point clouds.

While FIG. 2 shows two correspondences in the point clouds, it is typically required to have at least three correspondences to perform three-dimensional matching. However, a typical implementation uses for example several hundred correspondences for matching.

FIG. 3 shows a flow diagram of a first approach for tracking at least a part of the surface of the patient P.

Step S01 involves acquiring a first point cloud from the range camera 4 and a first thermal image from the thermographic camera 5 at a first point in time. In analogy, step S02 involves acquiring a second point cloud from the range camera 4 and a second thermal image from the thermographic camera 5 at a second point in time later than the first point in time.

Step S03 involves finding corresponding points in the first and second thermal images. This means that the positions of the pixels which image the same surface point are found in the two thermal images. Several algorithms for finding corresponding points in thermal images are known.

Step S04 involves obtaining correspondences from the first and second point clouds based on the corresponding points obtained from the thermal images. This means that points in the point clouds which represent the same surface point are identified from the corresponding points in the thermal images. As explained above, the correspondences can be found by geometrical considerations knowing the viewing directions and the properties of the range camera 4 and the thermographic camera 5. In particular, finding correspondences involves finding the point pair in the two point clouds which are found to be corresponding points in the thermal images. If there are no such points in the point clouds, a point pair forming a correspondence can be obtained by interpolating some or all of the points in a point cloud such that one or two interpolated points form the correspondence.

The result of step S04 are two reduced point clouds, that is a first reduced point cloud based on the first point cloud and a second reduced point cloud based on the second point cloud. The reduced point clouds only comprise point pairs which form correspondences.

Step S05 involves matching the correspondences, that is the first and second reduced point clouds, in order to obtain a transformation which transforms the first reduced point cloud into the second reduced point cloud. This transformation represents the movement of the surface of the patient P, which is therefore tracked. Matching the correspondences in step S05 thus is a 3D/3D matching for which many algorithms are known in the art.

The matching performed in step S05 is preferably a rigid fusion which does not change the locations of the points in the reduced point set relative to each other, but virtually moves the first reduced point cloud such that it best matches the second reduced point cloud.

FIG. 4 shows a flow diagram of a second approach for tracking the surface of the patient P. Step S11, S12 and S13 are equal to steps S01, S02, and S03, respectively, such that a detailed description of those steps is omitted.

Step S14 involves calculating a 3D model from the first point cloud and the first thermal image. This means that the positions of the corresponding points relative to the camera assembly 3 are determined, which at the same time means that the relative positions between the corresponding points can be calculated. The relative positions constitute the 3D model of the surface. The virtual position of the 3D model relative to the camera assembly 3 is known from the positions of the corresponding points relative to the camera assembly 3.

In other words, the 3D model represents samples of the surface and their relative positions as well as the position of the 3D model relative to the camera assembly 3, both at the first point in time.

Step S15 involves matching the 3D model to the second thermal image. This is a (rigid) 3D/2D matching which rotates and translates the 3D model relative to the camera assembly 3, and therefore relative to the thermographic camera 5, until a virtual image of the 3D model matches the second thermal image. This means that the positions of the pixels which image the points forming the 3D model in a virtual image, assuming the characteristics of the virtual imaging unit being identical to the characteristics of the thermal camera 5, equal the positions of the pixels which image the corresponding points in the second thermal image. A known algorithm which might be used in step S15 is for example the POSIT algorithm.

The invention claimed is:

1. A camera assembly for use in medical tracking applications, comprising:
a range camera configured to acquire a first point cloud of at least a portion of an object at a first moment in time and a second point cloud of at least the portion of the object at a second moment in time;
a thermographic camera configured to acquire a first thermal image of at least the portion of the object at the first moment in time and a second thermal image of at least the portion of the object at the second moment in time; and
a processor configured to calculate a movement of at least the portion of the object between the first moment of time and the second moment of time based on the first point cloud and the second point cloud with additional information acquired from the first and second thermal images.

2. The camera assembly of claim 1, the processor is further configured to identify, based on the additional information acquired from the first and second thermal images, a first point in the first point cloud and a second point in the second point cloud, wherein the first point and the second point correspond to a same point on the object.

3. The camera assembly of claim 2, wherein the processor is further configured to identify a thermal feature in the first thermal image and the second thermal image.

4. The camera assembly of claim 3, wherein the thermal feature is at least one of a temperature, a thermal signature of an area surrounding the same point of the object, a temperature distribution, a descriptor of a value for a property of the same point of the object, or a descriptor over a period of time.

5. The camera assembly of claim 2, wherein the movement is calculated based on the first point and the second point.

6. The camera assembly of claim 1, wherein the processor is further configured to generate a first reduced point cloud and a second reduced point cloud respectively associated with the first point cloud and the second point cloud, wherein the first reduced point cloud and the second reduced point cloud have a point-to-point correspondence, and wherein the first reduced point cloud and the second reduced point cloud are generated based on the first and second thermal images.

7. The camera assembly of claim 1, wherein the range camera and the thermographic camera are in a fixed relative position to one another.

8. The camera assembly of claim 1, wherein the first point cloud is a collection of points in a first image captured by the range camera that includes respective locations of points in the first image relative to the range camera and the second point cloud is a collection of points in a second image captured by the range camera that includes respective locations of points in the second image relative to the range camera.

9. The camera assembly of claim 1, further comprising a common housing in which the range camera and the thermographic camera are arranged.

10. The camera assembly of claim 1, wherein the range camera is a stereo camera, a structured light 3D scanner, a time-of-flight camera or a laser scanner.

11. The camera assembly of claim 1, further comprising a storage unit which stores calibration information which represents a relative position between the range camera and the thermographic camera.

12. The camera assembly of claim 1, wherein the processor is further configured to:
identify a first point pair including a first point in the first thermal image and a second point in the second thermal image, wherein the first point and the second point correspond to a same point on a surface of the object; and
map points of the first point pair to the first point cloud and the second point cloud, respectively, to provide a second point pair, wherein points of the first point pair and points of the second point pair correspond to the same point on the surface of the object.

13. The camera assembly of claim 12, wherein the processor is further configured to calculate the movement of at least the portion of the object based on the second point pair.

14. The camera assembly of claim 1, wherein the processor is further configured to determine a point-to-point correspondence, of at least one point, between the first point cloud and the second point cloud based on the additional information from the first and second thermal images, wherein the movement is calculated based on the point-to-point correspondence.

15. A method performed by a processor of a computer for tracking at least a part of a surface of an object, comprising the steps of:
acquiring, at the processor, at a first point in time, a first point cloud from a range camera and a first thermal image from a thermographic camera;

acquiring, at the processor, at a second point in time later than the first point in time, a second point cloud from the range camera and a second thermal image from the thermographic camera; and calculating a movement of at least the part of the surface of the object between the first moment of time and the second moment of time based on the first point cloud and the second point cloud with additional information acquired from the first and second thermal images.

16. The method of claim 15, wherein calculating the movement involves calibration information which represents a relative position between the range camera and the thermographic camera.

17. The method of claim 15, wherein calculating the movement involves matching, by the processor, at least a subset of the first point cloud and at least a subset of the second point cloud, the subsets of the point clouds comprising points respectively corresponding to same points on the surface of the object.

18. The method of claim 17, wherein matching the subsets of the point clouds utilizes the additional information acquired from the first and the second thermal images.

19. The method of claim 15, further comprising:

identifying a first point pair including a first point in the first thermal image and a second point in the second thermal image, wherein the first point and the second point correspond to a same point on the surface of the object; and mapping points of the first point pair to the first point cloud and the second point cloud, respectively, to provide a second point pair, wherein points of the first point pair and points of the second point pair correspond to the same point on the surface of the object.

20. A non-transitory computer-readable program storage medium storing a program which, when running on a computer, causes the computer to perform the steps of:

acquiring, at the computer, at a first point in time, a first point cloud from a range camera and a first thermal image from a thermographic camera;

acquiring, at the computer, at a second point in time later than the first point in time, a second point cloud from the range camera and a second thermal image from the thermographic camera; and calculating a movement of at least a part of a surface of an object between the first moment of time and the second moment of time based on the first point cloud and the second point cloud with additional information acquired from the first and second thermal images.

* * * * *